US012616971B2

(12) United States Patent
Zhang et al.

(10) Patent No.: US 12,616,971 B2
(45) Date of Patent: May 5, 2026

(54) SAMPLE PROCESSING AND DETECTION APPARATUS AND APPLICATION THEREOF

(71) Applicant: National Institute for Viral Disease Control and Prevention, Chinese Center for Disease Control and Prevention, Beijing (CN)

(72) Inventors: Xiaoguang Zhang, Beijing (CN); Xianhua Wang, Beijing (CN)

(73) Assignee: NATIONAL INSTITUTE FOR VIRAL DISEASE CONTROL AND PREVENTION, CHINESE CENTER FOR DISEASE CONTROL AND PREVENTION, Beijing (CN)

( * ) Notice: Subject to any disclaimer, the term of this patent is extended or adjusted under 35 U.S.C. 154(b) by 730 days.

(21) Appl. No.: 18/010,274

(22) PCT Filed: Jun. 21, 2021

(86) PCT No.: PCT/CN2021/101222
§ 371 (c)(1),
(2) Date: Dec. 14, 2022

(87) PCT Pub. No.: WO2021/245519
PCT Pub. Date: Dec. 23, 2021

(65) Prior Publication Data
US 2023/0294090 A1     Sep. 21, 2023

(30) Foreign Application Priority Data

Jun. 19, 2020     (CN) .......................... 202010565909.7

(51) Int. Cl.
*B01L 3/00*          (2006.01)
*B01L 7/00*          (2006.01)
(Continued)

(52) U.S. Cl.
CPC ........... *B01L 3/502715* (2013.01); *B01L 7/52* (2013.01); *C12Q 1/6851* (2013.01); *C12Q 1/701* (2013.01);
(Continued)

(58) Field of Classification Search
CPC ...... B01L 2300/0672; B01L 2300/044; A61M 5/28
See application file for complete search history.

(56) References Cited

U.S. PATENT DOCUMENTS 4,458,544 A      7/1984 Gyer et al.
6,780,617 B2     8/2004 Chen
(Continued)

FOREIGN PATENT DOCUMENTS

CN          108485912 A      9/2018
CN          110267744 A      9/2019

OTHER PUBLICATIONS

International Search Report and Written Opinion issued in PCT/CN2021/101222, mailed Sep. 24, 2021, 16 pages, with partial English translation.
(Continued)

*Primary Examiner* — Natalia Levkovich
(74) *Attorney, Agent, or Firm* — Buchanan Ingersoll & Rooney PC

(57)          ABSTRACT

A sample processing and detection apparatus and an application thereof, capable of efficiently implementing the entire detection process of extraction and amplification of a sample such as a pathogen nucleic acid in a short time, being safe and convenient.

17 Claims, 6 Drawing Sheets

(51) Int. Cl.
    *C12Q 1/6851*     (2018.01)
    *C12Q 1/70*      (2006.01)

(52) U.S. Cl.
    CPC ... *B01L 2200/0689* (2013.01); *B01L 2200/16* (2013.01); *B01L 2300/027* (2013.01); *B01L 2300/044* (2013.01); *B01L 2300/0672* (2013.01); *B01L 2400/0478* (2013.01)

(56)             References Cited

U.S. PATENT DOCUMENTS

| | | | |
|---|---|---|---|
| 2003/0129614 A1 | 7/2003 | Parameswaran et al. | |
| 2011/0151577 A1 | 6/2011 | Zhang et al. | |
| 2014/0134078 A1* | 5/2014 | Njoroge ............... | C12N 15/101 |
| | | | 422/527 |
| 2017/0292151 A1 | 10/2017 | Connolly et al. | |
| 2018/0164196 A1 | 6/2018 | Chen et al. | |
| 2018/0214864 A1 | 8/2018 | Lai et al. | |

OTHER PUBLICATIONS

The extended European Search Report issued May 15, 2024, by the European Patent Office in corresponding European Patent Application No. 21825975.2-1122. (8 pages).

* cited by examiner

SAMPLE PROCESSING AND DETECTION APPARATUS AND APPLICATION THEREOF

CROSS REFERENCE TO RELATED APPLICATIONS

This application is a U.S. National Phase Application of International Application No. PCT/CN2021/101222, titled "SAMPLE PROCESSING AND DETECTION APPARA-TUS AND APPLICATION THEREOF", filed on Jun. 21, 2021, which claims the benefit of priority to Chinese Patent Application No. 202010565909.7, titled "SAMPLE PRO-CESSING AND DETECTION APPARATUS AND APPLI-CATION THEREOF", filed with the China National Intel-lectual Property Administration on Jun. 19, 2020, the entire disclosures of which are incorporated herein by reference.

FIELD OF THE INVENTION

The present disclosure relates to the field of biological detection, and in particular to a sample processing and detection apparatus and application thereof.

BACKGROUND OF THE INVENTION

Infectious diseases are diseases caused by infectious pathogens infecting the human body. Because the pathogens are infectious, some infectious diseases can cause serious consequences (high fatality rate, serious complications, etc.), such as the coronavirus epidemic caused by the novel coronavirus infection of this time, for which early diagnosis is particularly important. Since there're no specific symp-toms in the early stage of most infectious pathogen infection, the early diagnosis of infectious diseases mainly relies on the detection of pathogens.

Pathogens mainly include viruses, bacteria, mycoplas-mas, etc., which mainly consist of nucleic acid molecules and protein molecules (antigens), and these two types of molecules are the target molecules for rapid pathogen detec-tion. Among them, the nucleic acid molecules of pathogens are the target molecules of nucleic acid detection. Different pathogens have different nucleic acid molecules. The nucleic acid fragments which are specifically designed are specifi-cally bound with pathogen molecules, and the nucleic acid molecules of pathogens can be detected by multiple methods such as PCR, RT-PCR, LAMP, and nucleic acid hybridiza-tion. Molecule detection plays an important role in infec-tious disease diagnosis, genetic disease diagnosis, cancer diagnosis, biochemical indicator detection and scientific research services. Conventional laboratory detection meth-ods are generally time-consuming and have many steps, which generally require multiple steps such as sample pretreatment, detection reaction, and result determination. To perform these steps, complex instruments, regulated lab space, and experienced operators are required. Rapid detec-tion of target molecules is required in many occasions, for example, rapid detection of cardiac markers is required in emergency clinics for cardiovascular disease, and the rapid identification of pathogenic microorganisms causing the sickness is required in fever clinics. In these occasions, complex experimental operations are difficult to be per-formed without necessary equipment and operators. There-fore, an integrated solution with simple operation and multi-step integration of sample processing, detection and result determination is urgently needed.

At present, the methods of rapid identification of patho-gens mainly include nucleic acid detection and immunological detection (antigen and/or antibody), where the nucleic acid detection generally includes steps such as sample pretreatment, nucleic acid amplification and result determi-nation, and the sample pretreatment includes four main steps, namely, lysing pathogens, adsorbing nucleic acid to solid phase, washing impurities and eluting nucleic acid from the adsorbed solid phase. In the whole process of the nucleic acid detection, the completion of these steps not only requires a series of reagents (chaotropic salts, pH buffer solution, inorganic salts, ethanol and other nucleic acid extraction reagents and amplification reagents) and support equipment (centrifuges, PCR instruments, automated work-stations, etc.), but also requires a specific experimental environment (a strictly divided three-zone nucleic acid amplification laboratory such as a specially designed PCR operation room) considering the possibility of nucleic acid contamination. In addition, due to the infectivity of patho-gens, biosafety issues (safety protection of operators and possible harm to the environment) should also be consid-ered. In addition, a complete nucleic acid detection based on PCR/RT-PCR generally takes more than 1 hour.

In order to improve the detection efficiency, integrated detection solutions have been developed. A commonly used integrated solution is to add different liquids (taking nucleic acid amplification as an example: sample lysis solution, magnetic beads, washing solution, eluent, amplification reaction solution) into small test tubes in rows, and using an electromagnetic rod to move in different test tubes to achieve the purpose of purifying nucleic acid and finally amplifying nucleic acid. This method is with an open system (the tube cover is open) and is thus prone to contamination. In addition, due to the large size of the instrument and the requirement for biosafety laboratories and other conditions, it is difficult to achieve rapid on-site detection in emergency clinics.

In a biological microfluidic chip, channels and sample pools for liquid flow and storage are formed on materials such as a glass sheet or an organic glass sheet by etching technology, the liquid flows in micro-sized channels under mechanical forces, magnetic forces or voltage, etc., to realize functions such as nucleic acid amplification, cell culture, and even chemical synthesis. The biological micro-fluidic chip has advantages such as high integration and small size, and it is suitable for solving the problem of rapid on-site detection.

However, the disadvantage of biological microfluidic chips is that the flow of liquid in tiny tubes (mm level or even smaller in size) is difficult to be controlled due to great influence of surface tension. In addition, the microfluidic chip also requires an external pump for power supply, so it is still an open system. If an integrated apparatus is desired with a drive apparatus needs to be considered, it is difficult to achieve miniaturization.

In 2004, Iquum Company applied for a patent for PCR by using a hose (U.S. Pat. No. 6,780,617B2, incorporated herein by reference). In this patent, different parts of the hose are squeezed mechanically to move the liquid inside the hose, and the liquid moves between different temperature modules, thereby performing nucleic acid amplification. Subsequently, Iquum Company applied for a series of related patents, in all of which compressible membrane is used to move liquid between different functional blocks under the action of external forces. The core thereof is that, one compressible hose is divided into several sections, and each section contains a different solution. The sections are separated by the effect of thermal bonding, and compressed by a mechanical force to achieve the purpose of moving the liquid flow. Disadvantages of this technology is that one hose can only perform 4-5 kinds of PCR, and if multiple fluorescence quantitative detection is required, the number of hoses needs to be increased, or the branches of the hose need to be increased.

The technical problem to be solved by those skilled in the art is to simplify the experimental operation steps of pathogen nucleic acid detection, reduce detection time and reduce biosafety risk, to realize "sample input, result output", which is also the core problem considered and solved by the present application.

SUMMARY OF THE INVENTION

In order to solve the above problems, a sample processing and detection apparatus is provided according to the present application.

In some embodiments of the present application, the apparatus is a nucleic acid extraction and detection apparatus, which includes a nucleic acid extraction unit and a nucleic acid amplification unit, where the nucleic acid extraction unit includes a micro-tube structure, and the liquid in the micro-tube is pushed to flow by a piston.

In some embodiments of the present application, the solution includes a lysis solution, a washing solution and an eluent, and the different solutions are located in different solution bottles respectively.

In some embodiments of the present application, the nucleic acid amplification unit comprises a PCR reaction well, and a PCR reaction element is placed in the PCR reaction well. Preferably, the PCR reaction element is powder.

In some embodiments of the present application, the temperature control module comprises one or more temperature modules for different temperature settings to realize the thermal cycling process of PCR.

In some embodiments of the present application, the apparatus further comprises a detection unit, which can collect signals from the nucleic acid amplification unit. Preferably, the detection unit comprises a fluorescence excitation and acquisition collection apparatus.

In some embodiments of the present application, the detection unit further includes a data processing module, via which the collected data is processed and directly displayed through a display screen.

A method for detecting nucleic acid by using the apparatus is further provided according to the present application, including:

adding a sample containing nucleic acid into a solution bottle with lysis solution;

adsorbing the nucleic acid on a substrate;

washing the nucleic acid adsorbed on the substrate with a washing solution;

eluting the nucleic acid adsorbed on the substrate with an eluent, and introducing the nucleic acid into PCR reaction wells; and making the PCR reaction wells be in direct contact with the temperature module, to carry out the PCR reaction.

In some embodiments of the present application, the method further includes detecting the signal of the PCR reaction wells, and analyzing the signal; preferably, the signal is a fluorescent signal.

In some embodiments of the present application, the sample containing nucleic acid is a sample containing pathogen, preferably a sample containing virus, *chlamydia, rickettsia, mycoplasma*, bacteria, spirochetes and fungi.

In some embodiments of the present application, the substrate is a membrane that can adsorb nucleic acid, preferably a silica gel membrane or a glass fiber membrane.

In other embodiments of the present application, the apparatus mainly includes two parts: a sample processing unit and a detection unit, where the sample processing unit and the detection unit may be in an integrated structure or may be in an operably connected structure.

In other embodiments of the present application, the apparatus is used for processing immunological detection samples, and the sample processing solution is a solution that dilutes the specimen and provides condition for immune reaction; the buffer solution is a washing solution, a labeling buffer, a substrate, and the like. The purpose thereof is to wash the impurities on the target molecule adsorption material such as immunomagnetic beads. The washed immunomagnetic beads are pushed into the detection unit by the liquid.

When the magnetic beads are used for nucleic acid detection and immunological detection, the magnetic beads may be placed in the sample processing solution.

The apparatus of the present application may further include a signal collection and processing unit, the detection module performs signal collection according to a predetermined program, and the collected data can be uploaded in a wireless manner. The signal detection unit may include a data processing module, the collected data is processed and directly displayed through a display screen.

The nucleic acid adsorption material may be any material that can adsorb nucleic acid, such as a large-pore silica gel filter membrane/filter element, or a glass fiber membrane, or particles containing silicon dioxide.

The nucleic acid detection may be performed in any conventional manner, for example, an amplification reaction, which may be isothermal amplification, or PCR or fluorescent quantitative PCR.

The detection may be a single-channel detection or a multi-target and multi-channel simultaneous detection.

The nucleic acid purification methods and amplification methods may be combined arbitrarily.

In other embodiments of the present application, the sample processing unit includes a syringe (1) and a main body (2);

where the main body (2) is provided with one or more solution chambers (21) arranged in a wheel shape, the solution chambers (21) surround to form a syringe movement cavity (25), each of the solution chambers (21) has a channel (22) at a bottom thereof, a silica gel sealing plug (23) is arranged at a contact surface between the channel (22) and the syringe movement cavity (25), and the channels (22) are arranged radially by taking a center of a bottom of the main body as a center a puncture needle (16) is provided at an end of the syringe (1) facing the syringe movement cavity (25), a push-pull rod (11) is provided at the other end of the syringe (1), and the syringe (1) further includes a shell (12); and the syringe (1) is located at a central axis of the main body (2) and is rotatable relative to the main body (2); the puncture needle (16) is not located at a geometric center of a bottom surface of the syringe.

In other embodiments of the present application, the bottom of the main body (2) is provided with a sample-adding channel (26), which is connected to the detection unit.

In other embodiments of the present application, a target adsorption material (15) is fixed at a position of a needle tubing, near the puncture needle (16), of the syringe (1), the target adsorption material (15) allows the liquid to pass through under a pressure condition, there is no gap between the target adsorption material (15) and a syringe cavity (17), and the liquid is not allowed to flow freely;

in a case that an external force is applied to a bottom of the push-pull rod (11), the syringe (1) moves toward the bottom of the main body (2), and the puncture needle (16) pierces the silica gel sealing plug (23); when the push-pull rod (11) is pushed or pulled, a solution in the solution chamber (21) passes through the target adsorption material (15), and the solution can pass in both directions according to a direction of pushing or pulling;

the syringe (1) is pulled away from the main body (2) to make the puncture needle (16) leave the silica gel sealing plug (23); the syringe (1) is rotated to make the puncture needle (16) be moved to the corresponding the silica gel sealing plug (23), and the operation is repeated.

In other embodiments of the present application, the number of the solution chambers (21) is one or more, preferably 1-20, such as 1, 2, 3, 4, 5, 6, 7, 8, 9, 10, 11, 12, 13, 14, 15, 16, 17, 18, 19 or 20. The solution chamber (21) is used for containing the same solution or different solutions.

In other embodiments of the present application, a top of the solution chamber (21) is provided with a silicone rubber plug (24), preferably, in a case that there are more than one silicone rubber plugs (24), the more than one silicone rubber plugs (24) are arranged on a silicone rubber cap (29), and in the silicone rubber cap (29), the more than one silicone rubber plugs are annularly arranged on a silica gel plane.

In other embodiments of the present application, the syringe (1) further includes a return spring (13) and a sealing ring (14).

In other embodiments of the present application, the target adsorption material (15) is a material that can adsorb nucleic acid, preferably a silica gel membrane or a glass fiber membrane.

In other embodiments of the present application, the target adsorption material (15) is a material that can adsorb protein.

In other embodiments of the present application, the target adsorption material (15) is in the form of a filter element or particles.

In other embodiments of the present application, the target adsorption material (15) is in the form of particles, the syringe (1) is provided with a filter screen (18) at a position near the puncture needle (16), and the filter screen (18) can obstruct the particulate adsorption material from entering the puncture needle (16).

In other embodiments of the present application, the detection unit includes a reaction tube (3), and the sample processing unit is in communication with the reaction tube (3) through a channel.

In other embodiments of the present application, the reaction tube (3) is pre-filled with a reaction reagent, preferably, the reaction reagent includes a reagent that can be used for a PCR reaction or an isothermal reaction.

In other embodiments of the present application, the detection unit further includes a signal collection part.

In other embodiments of the present application, the detection unit further includes a data processing part configured to process the data obtained by the signal collection part and display the processed data on a display screen.

The apparatus of the present application has the following features:

the storage of reagents and the movement of reagents in the tube are realized by using a piston-type liquid bottle;

the communications between the liquid bottle and the tube is realized by using a hollow needle to pierce the bottle mouth of the liquid bottle under the pressure of the piston;

the adsorption, washing and elution of nucleic acids, as well as immunological reactions, are achieved by using membranes or magnetic beads pre-positioned at specific positions in the tube;

the movement of the reaction solution between different temperature modules is achieved by pushing the solution.

In addition, by changing the arrangement manner of the liquid tubes, such as the type of cartridges of the revolver, the liquid chambers (sample, washing solution 1, washing solution 2, eluent, etc.) can be arranged in a cylinder, and the magnetic bead unit is put at the position of the gun barrel, so that the switching of different liquid flow paths is realized by rotating the sample chambers. One solution is to place the piston in the middle of the cylinder containing the reagent, and the piston is able to move up and down to generate positive or negative pressures, thereby realizing one-way or two-way flow of the liquid between the central piston and the reagent cylinder.

The apparatus of the present application has the following advantages: 1. The problems of storage and movement of the nucleic acid extraction reagents in the tube are solved by using a liquid bottle with a piston structure. 2. The problem that it is difficult for the liquid to flow in long-distance micro-channels is solved by using an etched tube to achieve liquid movement. 3. The liquid flow control is realized by the pre-set valves in the tube passage, so that the eluted nucleic acid solution can be distributed into different reaction wells, thereby realizing the integration of multiple PCR reaction units. 4. The matched case of the integrated apparatus is made of polymer material, metal material, or silica gel material, which is easy to be processed. 5. Double temperature control sections are designed, and the amplification mixed liquor is moved back and forth between the two temperature control sections to complete the amplification reaction, which reduces the amplification time compared with the traditional heating and cooling method of single temperature control. 6. The signal collection apparatus, such as the fluorescence collection apparatus, can get close to the PCR reaction section and make full use of the fluorescence intensity.

Through the above design, on the one hand, the fully enclosed automation of nucleic acid extraction is realized, and on the other hand, the nucleic acid amplification steps are optimized, which reduces the amplification time to a certain extent, and the detectable signal channels are increased, thereby increasing the number of detectable samples. In this case, the integration of nucleic acid extraction and amplification is realized as a whole.

BRIEF DESCRIPTION OF THE DRAWINGS

For more clearly illustrating embodiments of the present application, drawings referred to describe the embodiments will be briefly described hereinafter. Apparently, the drawings in the following description are only some examples of the present application, and for those skilled in the art, other embodiments may be obtained based on these drawings without any creative efforts.

Figure 1:
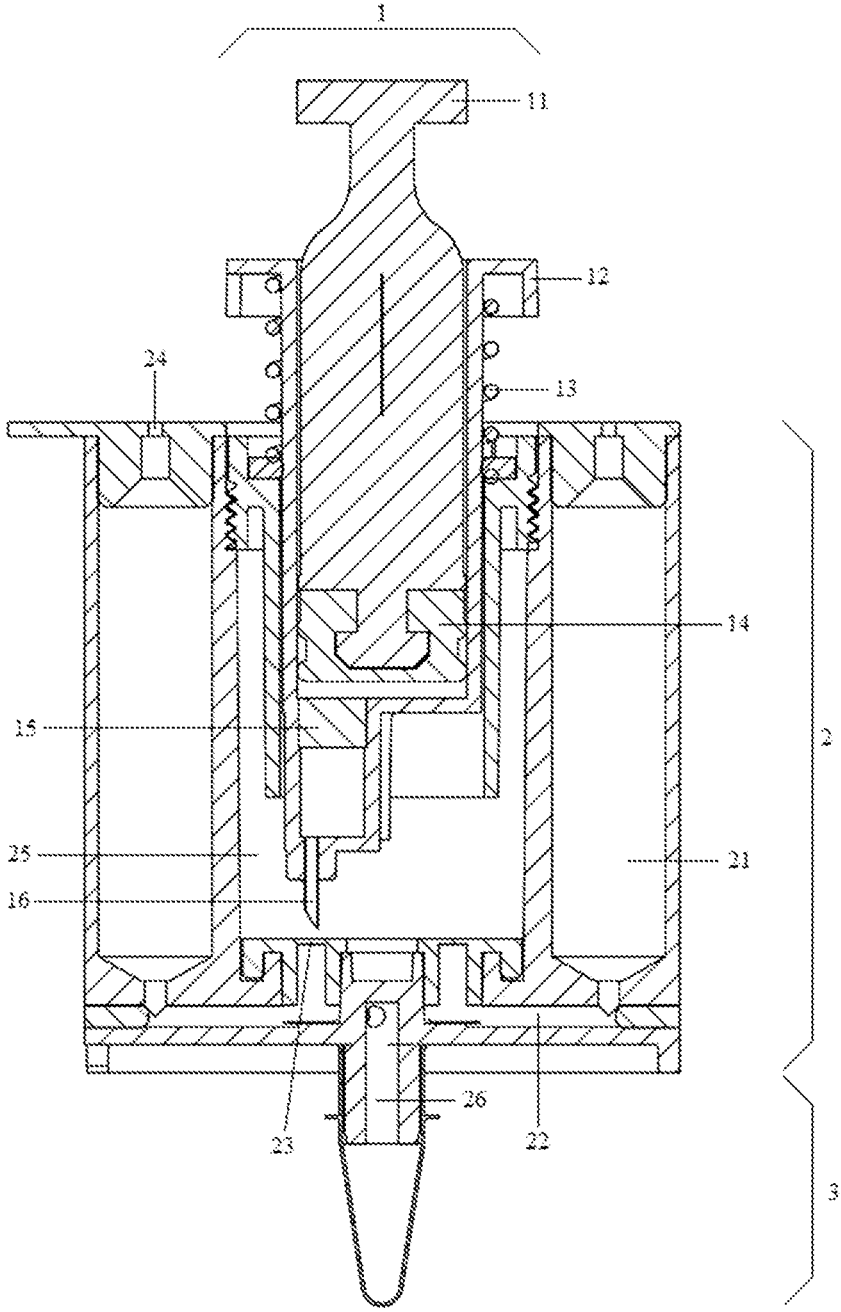
FIG. 1 is a schematic view of a sample processing and detection apparatus provided according to the present application.

Reference numerals in FIGS. 1 to 7 are as follows:

1: syringe
11: push-pull rod
12: syringe shell
13: return spring
14: sealing ring
15: target adsorption material
16: puncture needle
17: syringe cavity
18: filter screen
19: particulate adsorption material
2: case main body
21: solution chamber
211: bottom of solution chamber
212: round hole
22: channel
23: silica gel sealing plug
24: silicone rubber plug
25: syringe movement cavity
26: sample-adding channel
27, 28: fastener
29: silicone rubber cap
3: reaction tube

DETAILED DESCRIPTION OF THE EMBODIMENTS

Terms

Unless otherwise specified, terms used herein have the meanings commonly understood by those of ordinary skill in the art. For terms expressly defined herein, the meanings of such terms should be the described definitions.

Pathogen: It is a collective term for microorganisms and parasites that can cause disease. The microorganisms include viruses, *chlamydia, rickettsia, mycoplasma*, bacteria, spirochetes and fungi. In this application, pathogen primarily refers to pathogens that cause human disease.

Nucleic acid: It is a general term for deoxyribonucleic acid (DNA) and ribonucleic acid (RNA). It is a type of biopolymer, which is the most important substance in all biological molecules and widely exists in all animal and plant cells and microorganisms.

Nucleic acid extraction: In this applications, it refers to the process of extracting nucleic acid from pathogens by different methods using reagents and corresponding equipment.

Nucleic acid amplification: It refers to the amplification of specific nucleic acid sequences through the action of enzymes.

Primer: It refers to two fragments of artificially synthesized nucleotide sequences, which can be specifically bound to the single strand of the target nucleic acid fragment to be amplified. In the PCR reaction, primers can be designed and synthesized according to a fragment of nucleotide sequence of a known target gene. During the PCR amplification process, the target nucleic acid fragment is denatured by heat and then unwound into a single strand. After being cooled, the primer and the corresponding complementary sequence of the single strand are bound, then extension is performed under the action of a polymerase, and the cycle is repeated.

Target adsorption material refers to a substrate that can specifically adsorb a target. The target may be, for example, a nucleic acid, a protein, etc.; and the substrate may be in the form of a membrane, magnetic beads, colloid, or the like.

For those skilled in the art to better understand the solutions of the present application, the present application will be further described in detail below in conjunction with the drawings and specific embodiments.

In other embodiments of the present application, the sample processing and detection apparatus is in a wheel-shaped structure.

FIG. 1 shows a sample processing and detection apparatus according to an embodiment of the present application. The apparatus is a case, including a sample processing unit and a detection unit, which can be used for nucleic acid extraction and PCR detection. In this embodiment, the case (I) includes a nucleic acid extraction part (II) serving as the sample processing unit, and a reaction part (III) serving as the detection unit, which can be used for nucleic acid purification and amplification.

The nucleic acid extraction part (II) includes a syringe (1), a main body (2) with one or more solution chambers (21) arranged in a wheel shape and channels (22), a silica gel sealing plug (23) for sealing a contact surface between the channel (22) and the syringe movement cavity (25), a silicone rubber plug (24) for sealing a top of the solution chamber (21), a sample-adding channel (26), a reaction tube (3), etc.

The syringe includes a push-pull rod (11) capable of performing piston movement, a syringe shell (12), a syringe return spring (13), a syringe sealing ring (14), a target adsorption material (15), and a syringe puncture needle (16). Where, the puncture needle (16) is not located at a geometric center of a bottom surface of the syringe, but is located at a radial line with the geometric center as an origin. When the syringe is rotated relative to the case main body (2), the syringe puncture needle (16) makes an arc-shaped motion on the bottom of the case main body. The case main body (2) includes one or more hollow cylindrical solution chambers (21), the solution chambers are axially parallel to one another and parallel to a long axis of the case, and are arranged in a wheel shape with a hollow middle to form the syringe movement cavity (25). The syringe movement cavity (25) is used for inserting the syringe (1), a silica gel sealing ring (14) is sleeved outside the syringe, and the sealing ring (14) seals the front end of the syringe (including the part of the puncture needle (16)) and the hollow structure of the case, so that the front end of the syringe is isolated from the external environment to avoid pollution.

The solution chamber (21) may be one or more, for example 1, 2, 3, 4, 5, 6, 7, 8, 9, 10 or more, for containing solutions for nucleic acid purification and amplification reactions, such as lysis solution, washing solution and eluent. The bottom of the solution chamber (21) is conical and has a channel (22), the channel extends downward to be in communication with the corresponding transverse channel, and the transverse channels are arranged radially by taking the center of the bottom of the case as a center. Each of the channels is vertically upward at a position in a direction toward the center, and has an opening at a contact surface with the bottom of the syringe movement cavity (25), and the center of the opening coincides with the rotation track of the syringe puncture needle (16). The opening of the channel is sealed with a silicone rubber plug (23).

Figure 2:
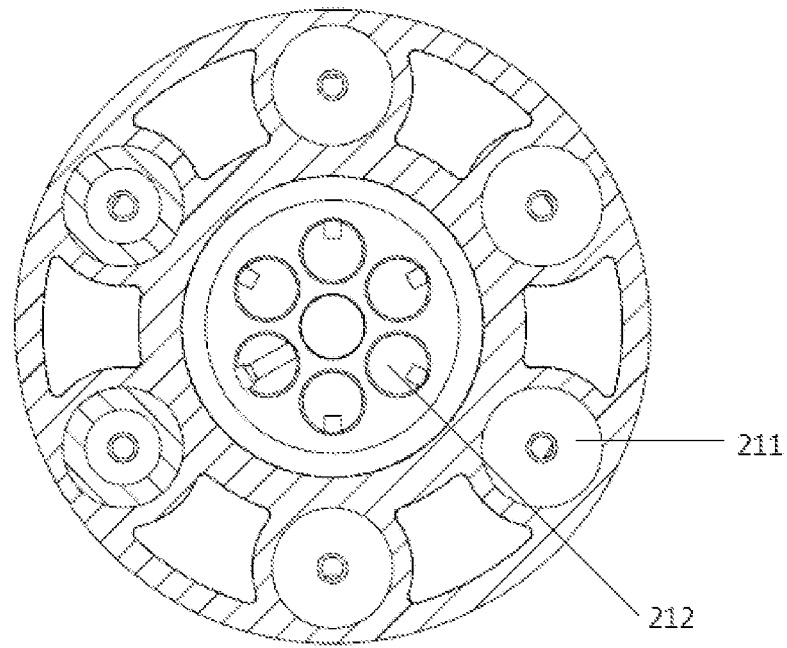
FIG. 2 is an internal top view of a bottom of a case main body provided according to the present application.

Taking a case main body with 6 solution chambers as an example, the internal top view of the bottom of the case main body is shown in FIG. 2. There are six circular holes (212) provided at the positions, corresponding to the reagent chamber, on the bottom of the solution chamber (211). The circular holes are vertically downward and are connected with six radial channels distributed horizontally. When the channels extend to a position below the reagent chamber, they extend vertically upward to be connected to the reagent chamber. Five of the six channels are connected to the reagent chamber, and the other one is connected to a vertically downward hole in the center, which is a sample-adding hole configured to be connected to an amplification tube.

Figure 3:
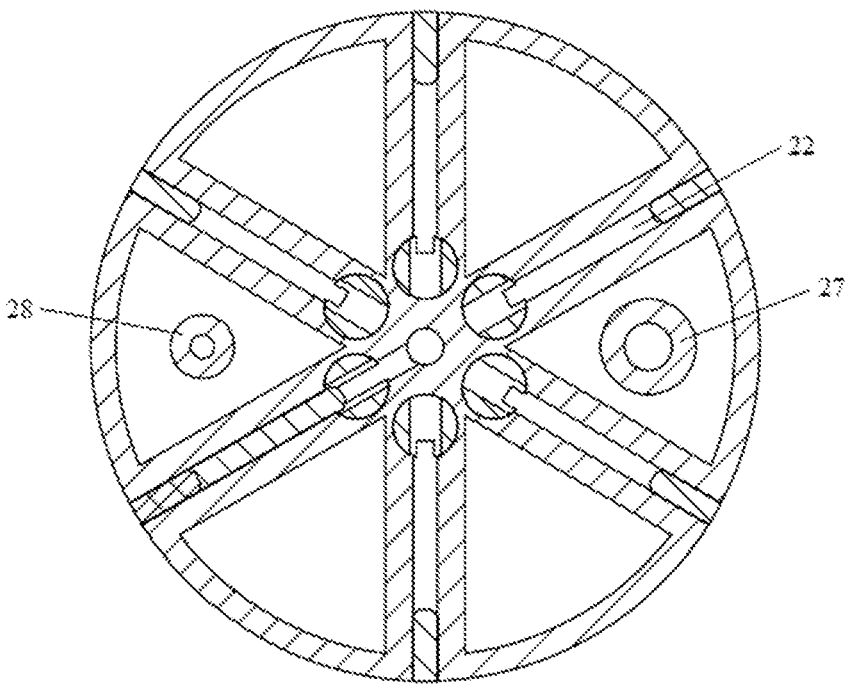
FIG. 3 is a schematic bottom view of the bottom of the cartridge main body provided according to the present application.

The bottom view of the bottom of the case main body is shown in FIG. 3. There are two short cylindrical fasteners (27, 28) with different diameters at the bottom of the case, which are used for positioning the case on an integrated machine. At positions for fixing the case of the integrated machine, there are two circular recesses with different diameters, which respectively corresponding to the two positioning cylinders on the case.

Figure 4A:
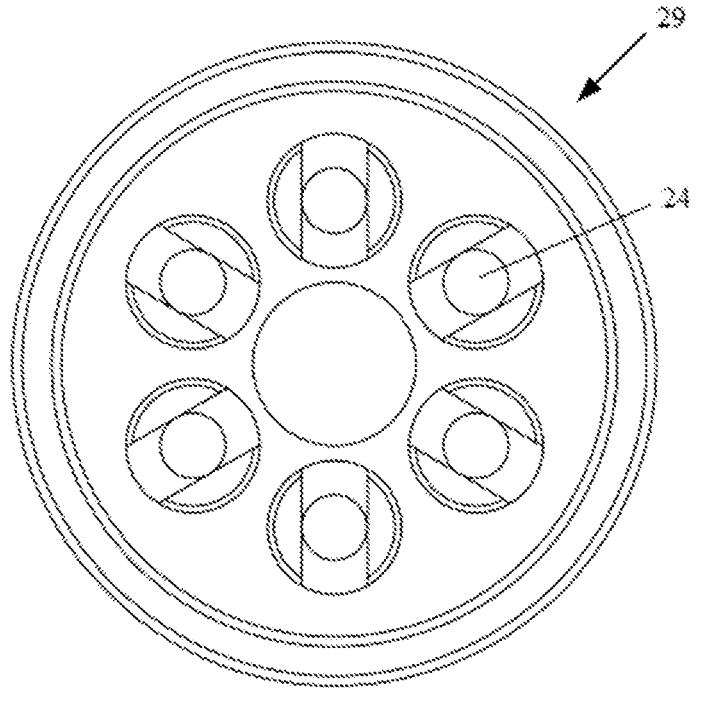
FIG. 4 is a plane view (A) and a side view (B) of a silica gel provided according to the present application.
Figure 4B:
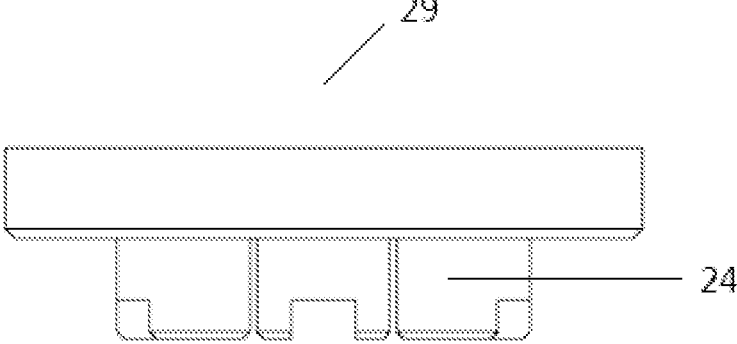

There is an opening at the top of the solution chamber (21), and a silicone rubber plug (24) is arranged at the opening. Different silicone rubber plugs corresponding to different solution chambers may be arranged on a silicone rubber cap (29) (FIG. 4). The silicone rubber cap is a plane with six hollow silica gel columns, and the positions of the hollow columns correspond to the six openings on the bottom of the case main body. The silicone rubber cap plays the role of sealing the solution chamber. In one embodiment of the present application, the opening at the top of the solution chamber (21) may be blocked with a filter element that can filter aerosols. The function of the filter element is to ensure that the air circulation, hence the air pressures inside and outside the chamber are the same, but the aerosols is not allowed to pass through, so as to avoid contamination.

Figure 5:
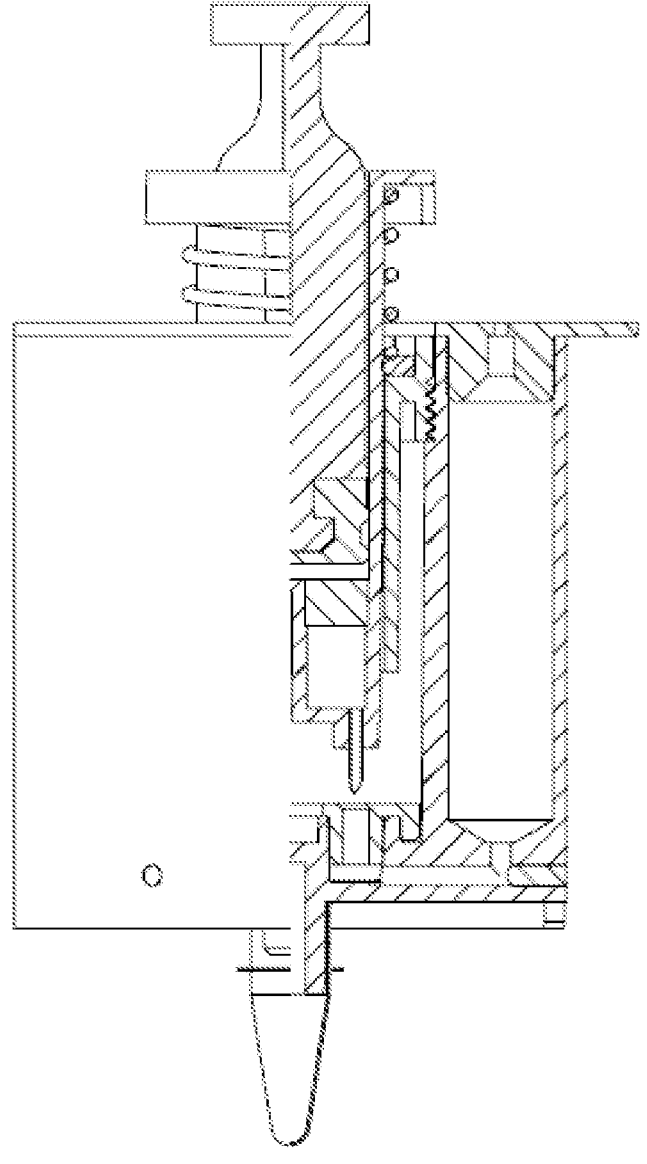
FIG. 5 is a half-section schematic view showing the sample processing and detection apparatus provided according to the present application.
Figure 6:
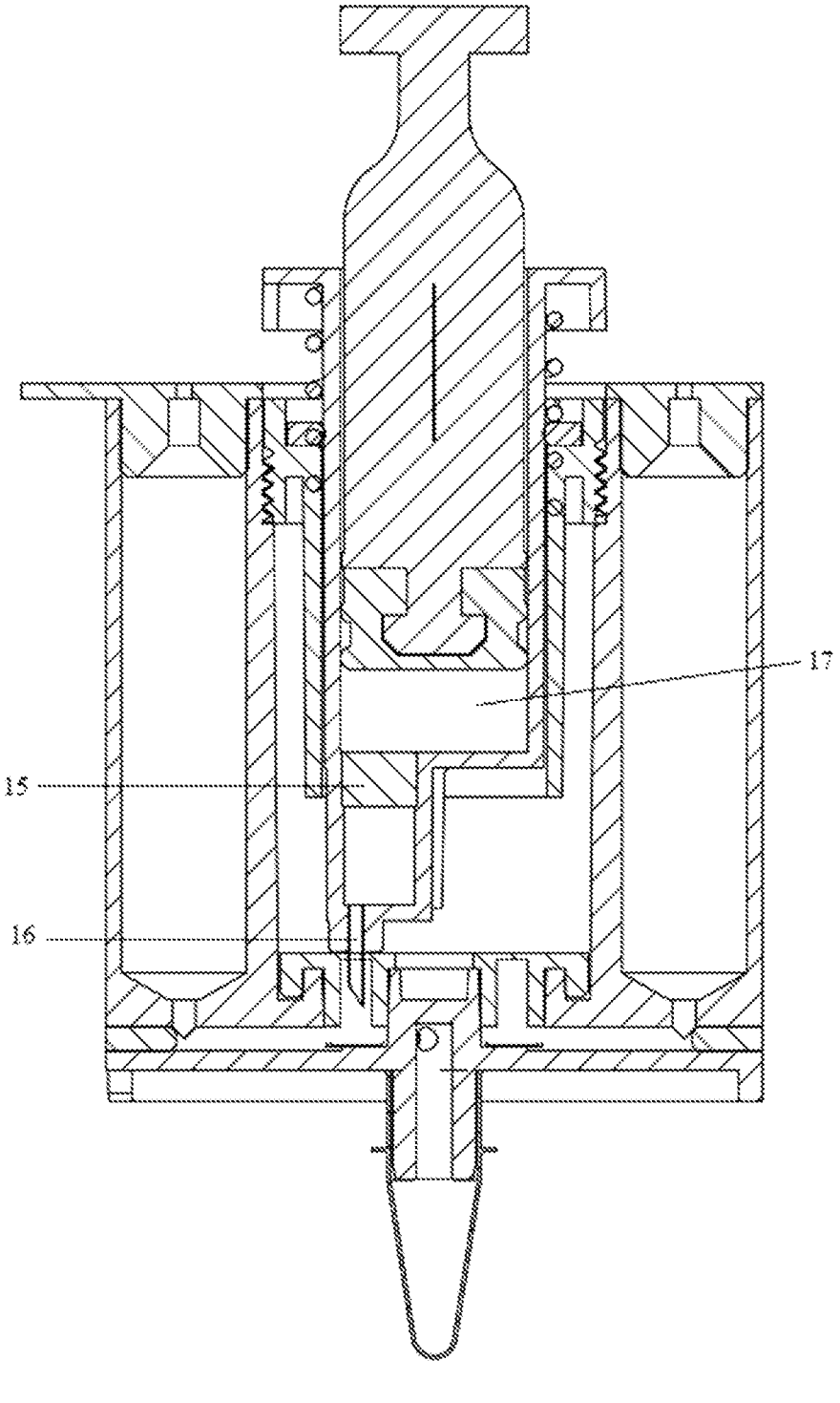
FIG. 6 is a schematic view showing the puncture needle piercing a channel to communicate a syringe cavity with a channel of a solution chamber.
Figure 7:
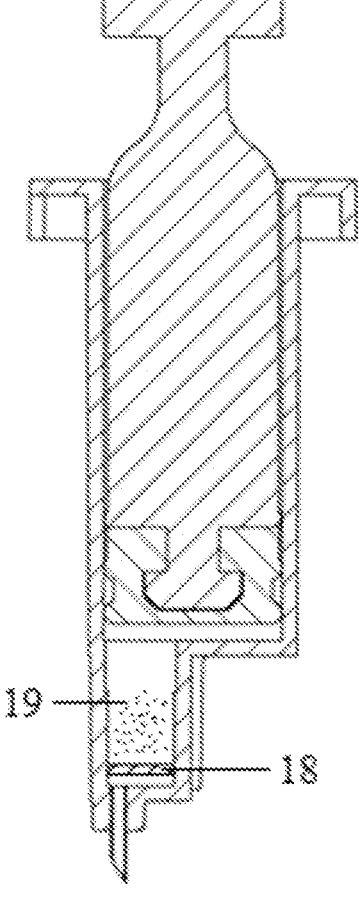
FIG. 7 is a schematic view showing the structure of a head of a syringe when the target adsorption material in the form of magnetic beads is used.

FIG. 5 shows a half-sectional view of a sample processing and detection apparatus according to an embodiment of the present application. When the syringe is rotated to a certain angle, the puncture needle (16) is aligned with the circular hole below, by pressing the syringe downward, the puncture needle (16) pierces the silicone rubber cap, so that the syringe is in communication with the reagent chamber. The syringe piston rod is pulled and pressed to generate negative and positive pressures to drive the solution in the reagent chamber, or the solution in the syringe to flow between the syringe and the solution chamber, where the flow may be unidirectional or bidirectional.

The nucleic acid extraction part includes a syringe for sucking liquid and several solution chambers containing different solution components. The syringe includes a barrel wall, a piston, a pull rod and the like. The bottom of the syringe is provided with a material that can adsorb nucleic acid, such as a filter membrane or filter element containing silicon dioxide components; or is provided with a filter membrane that can block the passage of magnetic beads or glass beads for nucleic acid purification. The syringe can be rotated, swayed, etc. to align the tip with the sealing cap of the solution chamber. The piston in the syringe is moved up and down to achieve the function of sucking and discharging liquid. The syringe can be moved as a whole in parallel with an axial direction of the syringe. The tip of the syringe pierces the sealing caps of different solution chambers to complete the communication between the syringe and the solution chambers. Through the suction and discharge by the syringe, the liquid moves back and forth between the syringe and the solution chambers, so as to realize functions such as evenly mixing, filtering and washing of the solution. During the nucleic acid purification process, the syringe first pierces into the solution chamber containing the lysis solution and the specimen, the piston is moved up and down to guide the solution to pass through the nucleic acid adsorption material, and to evenly mix the solution simultaneously. The other solution chambers respectively contain washing solution, nucleic acid eluent, and solutions required for nucleic acid amplification. The solution chambers may be arranged around the syringe, or sequentially arranged on a plane, or arranged in groups. When the solution chambers are arranged around the syringe, the solution outlets are arranged in a ring, and the outlets are sealed by silica gel or other materials. The syringe is arranged on an eccentric shaft of an inner cylinder inside the case, and the puncture needle (16) is positioned at the outlets of different solution chambers through the rotation of the syringe on the eccentric shaft. Alternatively, the puncture needle (16) of the syringe is placed at a position other than the center of the circle of the bottom surface of the syringe, and the syringe is placed coaxially inside the case, in this case, the puncture needle (16) may be positioned at the outlets of different solution chambers through the rotation of the syringe.

The detection unit of the apparatus of the present application may be a nucleic acid amplification part, including an amplification section that can be pushed back and forth, a temperature control module and a fluorescence detection module. The eluted nucleic acid molecules are introduced to the amplification section, to be mixed with the amplification dry powder pre-set in this section for fully dissolution. Then the amplification reaction is carried out according to the predetermined program, where the temperature control module provides an appropriate temperature and reaction time, and the fluorescence detection module collects fluorescence signals according to the predetermined program. The collected data is displayed in a brief manner and can be uploaded via Bluetooth.

In one embodiment, the sample-adding channel (26) and the amplification tube (3) correspond to the temperature control module of the integrated apparatus. When the case is placed on the integrated apparatus, the amplification tube fully contacts with the temperature control module. The opening of each sample chamber is covered with a silica gel membrane having an opening in the middle, and the opening on the silica gel membrane is blocked with a filter element that can filter aerosols. The function of the filter element is to ensure the air circulation, and the air pressures inside and outside the sample chamber is consistent, but the aerosols is not allowed to pass through, so as to avoid contamination.

The above apparatus has the following advantages:

1. Different solution chambers are pierced by positioning by using rotation of the syringe, to realize the switching of different solutions, thus the use of tiny flow paths and valves are avoided, which makes the structure simple and reliable.

2. The movement of liquid is realized by using the positive and negative pressures generated by pulling and pushing the syringe, which solves the problem of difficult liquid flow in long-distance micro-channels.

3. The nucleic acid adsorption material is fixed on the bottom of the syringe, so that the liquid flow and the nucleic acid adsorption, washing impurities and other processes are completed synchronously. The design is simple and reliable.

4. Meanwhile, the syringe can be used as a pipetting apparatus for precise suction and transfer of solution, and it can also be used as a mixing apparatus for mixing and configuring incompatible components.

5. The solution chambers are arranged in a circular ring in the case, which makes full use of the space, so that overall volume is small.

6. With the above design, on the one hand, the fully enclosed automation of nucleic acid extraction is realized, and on the other hand, the nucleic acid amplification steps are optimized, which reduces the amplification time to a certain extent, and the detectable fluorescence channels are increased, thereby increasing the number of detectable pathogens. In this case, the integration of extraction and amplification of pathogen nucleic acid is realized as a whole.

First Embodiment: Fluorescent Quantitative PCR

A case with 6 solution chambers (21) is taken as an example. The solution chambers No. 1-3 of the case were respectively filled with 500 microliters of lysis solution, 800 microliters of washing solution 1, and 800 microliters of washing solution 2, the solution chamber No. 4 was not filled with any reagents or solutions, and the solution chamber No. 5 was filled with 200 microliters of eluent. A fluorescent quantitative PCR reaction system containing the novel coronavirus was added to the amplification tube.
Experimental Process 1) Adding sample: A nasopharyngeal swab dipped with specimen was inserted into the solution chamber No. 1, stirred for 10 seconds, and broken off, then the lid was closed. Or the nasopharyngeal swab was taken out, discarded in a garbage bag, and disposed according to bio-safety-related procedures. Or 200 microliters of sample solution was added, and the lid was closed.

2) Adsorbing nucleic acid: The syringe (1) was rotated to align the puncture needle (16) with the silicone rubber cap corresponding to the solution chamber No. 1, then the syringe (1) was pressed down to pierce the silicone rubber cap, and the push-pull rod (11) was pulled and pressed down, so that the lysis solution was driven by the pressure to repeatedly pass through the nucleic acid adsorption material fixed at the bottom of the syringe (1). After 10 times of pulling and pressing, the syringe (1) was pressed down to push all the solution back to the solution chamber No. 1.

3) Washing impurities: The syringe (1) was rotated to align the puncture needle (16) with the silicone rubber cap corresponding to the tube No. 2, then the syringe (1) was pressed downward to pierce the silicone rubber cap, and the push-pull rod (11) was pulled and pressed downward, so that the washing solution 1 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 2.

4) Washing impurities: The syringe (1) was rotated to align the puncture needle (16) with the silicone rubber cap corresponding to the tube No. 3, then the syringe (1) was pressed downward to pierce the silicone rubber cap, and the push-pull rod (11) was pulled and pressed downward, so that the washing solution 2 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 3.

5) Drying nucleic acid adsorption material: The syringe (1) was rotated to align the puncture needle (16) with the silicone rubber cap corresponding to the solution chamber No. 4, then the syringe (1) was pressed downward to pierce the silicone rubber cap, and the push-pull rod (11) was pulled and pressed downward. The solution chamber No. 4 was an empty tube, the air was driven by the pressure to repeatedly pass through the nucleic acid adsorption material fixed at the bottom of the syringe (1), the purpose is to volatilize the residual washing solution 2 into the air, to dry the nucleic acid adsorption material.

6) Eluting nucleic acid: The syringe (1) was rotated to align the puncture needle (16) with the silicone rubber cap corresponding to the solution chamber No. 5, then the syringe (1) was pressed downward to pierce the silicone rubber cap, and the push-pull rod (11) was pulled and pressed downward, so that the TE solution was driven by the pressure to repeatedly pass through the nucleic acid adsorption material fixed at the bottom of the syringe (1), so as to elute the nucleic acid on the adsorption material into the TE solution. After 10 times of pulling and pressing, the syringe (1) was not pressed down, and all the solution is remained in the syringe (1).

7) Adding sample: The syringe (1) was rotated to align the puncture needle (16) with the silicone rubber cap corresponding to the solution chamber No. 6, then the syringe (1) was pressed downward to pierce the silicone rubber cap, and the push-pull rod (11) was pulled and pressed downward, so that the TE solution containing nucleic acid was driven by the pressure to pass through the central channel to enter the nucleic acid amplification tube, in which the TE solution was mixed with the prepared fluorescent PCR reaction system to complete the sample addition.

8) Amplification detection: The temperature module was controlled to perform the following procedures: reverse transcription (50° C. for 10 minutes); pre-denaturation (95° C. for 60 seconds); amplification reaction (95° C. for 10 seconds, 65° C. for 10 seconds, fluorescence collection at 65° C., 40 cycles).

Second Embodiment: Florescent Quantitative PCR
of Premixed Novel Coronavirus Nucleic Acid The solution chambers No. 1-3 (21) of a case were respectively filled with 500 microliters of lysis solution (component), 800 microliters of washing solution 1, and 800 microliters of washing solution 2, the solution chamber No. 4 was filled with 200 microliters of eluent, and the solution chamber No. 5 was filled with lyophilized powder of the novel coronavirus amplification reaction system. The amplification tube was empty.
Experimental Process 1) Adding sample: A nasopharyngeal swab dipped with specimen was inserted into the solution chamber No. 1, stirred for 10 seconds, and broken off, then the lid was closed. Or the nasopharyngeal swab was taken out, discarded in a garbage bag, and disposed according to bio-safety-related procedures. Or 200 microliters of sample solution was added, and the lid was closed.

2) Adsorbing nucleic acid: The syringe (1) was rotated to align the puncture needle (16) with the silicone rubber cap corresponding to the solution chamber No. 1, then the syringe (1) was pressed downward to pierce the silicone rubber cap, and the push-pull rod (11) was pulled and pressed downward, so that the lysis solution was driven by the pressure to repeatedly pass through the nucleic acid adsorption material fixed at the bottom of the syringe (1). After 10 times of pulling and pressing, the syringe (1) was pressed downward to push all the solution back to the solution chamber No. 1.

3) Washing impurities: The syringe (1) was rotated to align the puncture needle (16) with the silicone rubber cap corresponding to the solution chamber No. 2, then the syringe (1) was pressed downward to pierce the silicone rubber cap, and the push-pull rod (11) was pulled and pressed downward, so that the washing solution 1 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 2.

4) Washing impurities: The syringe (1) was rotated to align the puncture needle (16) with the silicone rubber cap corresponding to the solution chamber No. 3, then the syringe (1) was pressed downward to pierce the silicone rubber cap, and the push-pull rod (11) was pulled and pressed downward, so that the washing solution 2 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 3.

5) Drying the nucleic acid adsorption material: The syringe (1) was lifted to suspend the puncture needle (16) in the movement cavity (25) of the syringe (1), then the push-pull rod (11) was pulled and pressed downward, so that the air was driven by the pressure to repeatedly pass through the nucleic acid adsorption material fixed at the bottom of the syringe (1), so as to discharge the residual washing solution 2 in the nucleic acid adsorption material into the air in the movement cavity (25) of the syringe (1) to dry the nucleic acid adsorption material.

6) Eluting nucleic acid: The syringe (1) was rotated to align the puncture needle (16) with the silicone rubber cap corresponding to the solution chamber No. 4, then the syringe (1) was pressed downward to pierce the silicone rubber cap, and the push-pull rod (11) was pulled and pressed downward, so that the TE solution was driven by the pressure to repeatedly pass through the nucleic acid adsorption material fixed at the bottom of the syringe (1), so as to elute the nucleic acid on the adsorption material into the TE solution. After 10 times of pulling and pressing, the syringe (1) was not pressed downward, and all solution was remained in the syringe (1).

7) Mixing the reaction system: The syringe (1) was rotated to align the puncture needle (16) with the silicone rubber cap corresponding to the solution chamber No. 5, then the syringe (1) was pressed downward to pierce the silicone rubber cap, and the push-pull rod (11) was pressed downward, so that the TE solution containing nucleic acid was driven by the pressure to pass through the flow path of the solution chamber (21), the TE solution was mixed with the prepared fluorescent PCR reaction system, and then the push-pull rod (11) was repeatedly pushed and pulled to fully mix the TE and the reaction system.

8) Adding sample: The syringe (1) was lifted and rotated to align the puncture needle (16) with the silicone rubber cap corresponding to the solution chamber No. 6, then the syringe (1) was pressed downward to pierce the silicone rubber cap, and the push-pull rod (11) was pressed downward, so that the well mixed reaction system passed through the flow path channel and entered the nucleic acid amplification tube to complete the sample addition.

9) Amplification detection: The temperature module was controlled to perform the following procedures: reverse transcription (50° C. for 10 minutes); pre-denaturation (95° C. for 60 seconds); amplification reaction (95° C. for 10 seconds, 65° C. for 10 seconds, fluorescence collection at 65° C., 40 cycles).

Third Embodiment: Isothermal Amplification Experiment of Premixed Novel Coronavirus Nucleic Acid The solution chambers No. 1-3 (21) of a case were respectively filled with 500 microliters of lysis solution, 800 microliters of washing solution 1, and 800 microliters of washing solution 2, the solution chamber No. 4 was filled with 200 microliters of eluent, and the solution chamber No. 5 (21) was filled with the redissolving solution of the isothermal amplification reaction system of the novel coronavirus. The amplification tube was filled with lyophilized powder of the isothermal amplification system.

Experimental Process

1) Adding sample: A nasopharyngeal swab dipped with specimen was inserted into the solution chamber No. 1, stirred for 10 seconds, and broken off, then the lid was closed. Or the nasopharyngeal swab was taken out, discarded in a garbage bag, and disposed according to biosafety-related procedures. Or 200 microliters of sample solution was added, and the lid was closed.

2) Adsorbing nucleic acid: The syringe (1) was rotated to align the puncture needle (16) with the silicone rubber cap corresponding to the solution chamber No. 1, then the syringe (1) was pressed downward to pierce the silicone rubber cap, and the push-pull rod (11) was pulled and pressed downward, so that the lysis solution was driven by the pressure to repeatedly pass through the nucleic acid adsorption material fixed at the bottom of the syringe (1). After 10 times of pulling and pressing, the syringe (1) was pressed downward to push all the solution back to the solution chamber No. 1.

3) Washing impurities: The syringe (1) was rotated to align the puncture needle (16) with the silicone rubber cap corresponding to the solution chamber No. 2, then the syringe (1) was pressed downward to pierce the silicone rubber cap, and the push-pull rod (11) was pulled and pressed downward, so that the washing solution 1 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 2.

4) Washing impurities: The syringe (1) was rotated to align the puncture needle (16) with the silicone rubber cap corresponding to the solution chamber No. 3, then the syringe (1) was pressed downward to pierce the silicone rubber cap, and the push-pull rod (11) was pulled and pressed downward, so that the washing solution 2 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 3.

5) Drying the nucleic acid adsorption material: The syringe (1) was lifted to suspend the puncture needle (16) in the shell of the syringe (1), then the push-pull rod (11) was pulled and pressed downward, so that the air was driven by the pressure to repeatedly pass through the nucleic acid adsorption material fixed at the bottom of the syringe (1), so as to discharge the residual washing solution 2 in the nucleic acid adsorption material into the air of the shell of the syringe (1) to dry the nucleic acid adsorption material.

6) Eluting nucleic acid: The syringe (1) was rotated to align the puncture needle (16) with the silicone rubber cap corresponding to the solution chamber No. 4, then the syringe (1) was pressed downward to pierce the silicone rubber cap, and the push-pull rod (11) was pulled and pressed downward, so that the TE solution was driven by the pressure to repeatedly pass through the nucleic acid adsorption material fixed at the bottom of the syringe (1), so as to elute the nucleic acid on the adsorption material into the TE solution. After 10 times of pulling and pressing, the syringe (1) was not pressed downward, and all solution is remained in the syringe (1).

7) Mixing the reaction system: The syringe (1) was rotated to align the puncture needle (16) with the silicone rubber cap corresponding to the solution chamber No. 5, then the syringe (1) was pressed downward to pierce the silicone rubber cap, and the push-pull rod (11) was pressed downward, so that the TE solution containing nucleic acid was driven by the pressure to pass through the flow path of the solution chamber (21), through which the TE solution was mixed with the prepared redissolving solution of the isothermal amplification reaction system, and then the push-pull rod (11) was repeatedly pushed and pulled to fully mix the TE and the redissolving solution.

8) Adding sample: The syringe (1) was lifted and rotated to align the puncture needle (16) with the silicone rubber cap corresponding to the solution chamber No. 6, then the syringe (1) was pressed downward to pierce the silicone rubber cap, and the push-pull rod (11) was pressed downward, so that the well mixed redissolving solution system passed through the flow path channel and entered the amplification tube pre-filled with the lyophilized powder of isothermal amplification to complete the sample addition 9) Amplification detection: The temperature module was controlled to perform the following procedures: 39° C. for 10 minutes, fluorescence collection.

The nucleic acid adsorption material may be a large-pore silica gel filter membrane/filter element or a particulate adsorption material (19), such as particles containing silicon dioxide. When the silicon dioxide particles were used, a filter screen was provided at the connection part between the bottom of the syringe (1) and the puncture needle (16), to block the passage of the particles, see FIG. 7.

Fourth Embodiment: Nucleic Acid Purification by Using Large-Pore Silica Gel Filter Membrane/Filter Element, and Fluorescent Quantitative PCR Detection of Novel Coronavirus The solution chambers No. 1-3 (21) of a case were respectively filled with 500 microliters of lysis solution, 800 microliters of washing solution 1, and 800 microliters of washing solution 2, the solution chamber No. 4 (21) was not filled with any reagents or solutions, and the solution chamber No. 5 was filled with 200 microliters of eluent. The amplification tube was filled with a fluorescent quantitative PCR reaction system containing the novel coronavirus. In the cylinder at the bottom of the syringe (1), a large-pore silica gel filter element or a large-pore silica gel filter membrane with the same diameter as the inner diameter of the cylinder was installed. When the filter membrane was used, a retaining ring for fixing the filter membrane needed to be pre-installed in the cylinder.

Reagent Formula:

Lysis solution: 4M guanidinium isothiocyanate, 0.5% NP40, 50 mM Tris·Cl (pH5.5), 10 mM EDTA;

Washing solution 1: A buffering solution containing ethanol or isopropanol, which generally had a composition of 10 mM Tris-HCl (pH 7.5) and 80% ethanol.

Washing solution 2: A solution containing higher concentration of ethanol or isopropanol, which generally had a composition of 100% ethanol.

Washing solution formula without using reagents such as ethanol or isopropanol.

Eluent: TE solution, which had a composition of 10 mM Tris and 0.1 mM EDTA (pH 8.5).

1) Adding sample: A nasopharyngeal swab dipped with specimen was inserted into the solution chamber No. 1, stirred for 10 seconds, and broken off, then the lid was closed. Or the nasopharyngeal swab was taken out, discarded in a garbage bag, and disposed according to bio-safety-related procedures. Or 200 microliters of sample solution was added, and the lid was closed.

2) Adsorbing nucleic acid: The syringe (1) was rotated to align the puncture needle (16) with the silicone rubber cap corresponding to the solution chamber No. 1, then the syringe (1) was pressed down to pierce the silicone rubber cap, and the push-pull rod (11) was pulled and pressed downward, so that the lysis solution was driven by the pressure to repeatedly pass through the nucleic acid adsorption material fixed at the bottom of the syringe (1). After 10 times of pulling and pressing, the syringe (1) was pressed downward to push all the solution back to the solution chamber No. 1.

3) Washing impurities: The syringe (1) was rotated to align the puncture needle (16) with the silicone rubber cap corresponding to the solution chamber No. 2, then the syringe (1) was pressed downward to pierce the silicone rubber cap, and the push-pull rod (11) was pulled and pressed downward, so that the washing solution 1 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 2.

4) Washing impurities: The syringe (1) was rotated to align the puncture needle (16) with the silicone rubber cap corresponding to the solution chamber No. 3, then the syringe (1) was pressed downward to pierce the silicone rubber cap, and the push-pull rod (11) was pulled and pressed downward, so that the washing solution 2 was driven by the pressure to repeatedly pass through the nucleic acid adsorption material fixed at the bottom of the syringe (1). After 10 times of pulling and pressing, the syringe (1) was pressed downward to push all the solution back to the solution chamber No. 3.

5) Drying the nucleic acid adsorption material: The syringe (1) was lifted to suspend the puncture needle (16) in the movement cavity (25) of the syringe (1), then the push-pull rod (11) was pulled and pressed downward, so that the air was driven by the pressure to repeatedly pass through the nucleic acid adsorption material fixed at the bottom of the syringe (1), so as to discharge the residual washing solution 2 in the nucleic acid adsorption material into the air of the movement cavity (25) of the syringe (1) to dry the nucleic acid adsorption material.

6) Eluting nucleic acid: The syringe (1) was rotated to align the puncture needle (16) with the silicone rubber cap corresponding to the solution chamber No. 4, then the syringe (1) was pressed downward to pierce the silicone rubber cap, and the push-pull rod (11) was pulled and pressed downward, so that the TE solution was driven by the pressure to repeatedly pass through the nucleic acid adsorption material fixed at the bottom of the syringe (1), so as to elute the nucleic acid on the adsorption material into the TE solution. After 10 times of pulling and pressing, the syringe (1) was not pressed downward, and all solution is remained in the syringe (1).

7) Mixing the reaction system: The syringe (1) was rotated to align the puncture needle (16) with the silicone rubber cap corresponding to the solution chamber No. 5, then the syringe (1) was pressed downward to pierce the silicone rubber cap, and the push-pull rod (11) was pressed downward, so that the TE solution containing nucleic acid was driven by the pressure to pass through the flow path of the solution chamber (21), the TE solution was mixed with the prepared fluorescent PCR reaction system, and then the push-pull rod (11) was repeatedly pushed and pulled to fully mix the TE and the reaction system.

8) Adding sample: The syringe (1) was lifted and rotated to align the puncture needle (16) with the silicone rubber cap corresponding to the solution chamber No. 6, then the syringe (1) was pressed downward to pierce the silicone rubber cap, and the push-pull rod (11) was pressed downward, so that the well mixed reaction system passed through the flow path channel and entered the nucleic acid amplification tube to complete the sample addition.

9) Amplification detection: The temperature module was controlled to perform the following procedures: reverse transcription (supplement time and temperature); pre-denaturation (supplement time and temperature); amplification reaction (95° C. for 10 seconds, 65° C. for 10 seconds, fluorescence collection at 65° C., 40 cycles).

Fifth Embodiment: Nucleic Acid Purification by Using Silicon Dioxide Particles, and Fluorescent Quantitative PCR Detection of Novel Coronavirus In the apparatus of this embodiment, the target adsorption material (008) was in the form of particles, and the syringe (1) was provided with a filter screen (18) at the position near the puncture needle (16), where the filter screen (18) can block the particulate adsorption material from entering the puncture needle (16), see FIG. 7.

Other experimental operations were similar to the fourth embodiment.

The sample processing and detection apparatus provided by the present application has been described in detail above. The principles and implementations of the present application are described herein by using specific examples, and the descriptions of the above examples are only used to help understanding of the method and the core concept of the present application. It should be noted that for those of ordinary skill in the art, several improvements and modifications can also be made to the present application without departing from the principle of the present application, and these improvements and modifications also fall within the protection scope of the claims of the present application.

The invention claimed is:

1. A sample processing and detection apparatus, comprising a syringe and a main body, wherein the main body is provided with a plurality of solution chambers arranged circumferentially, and a syringe movement cavity surrounded by the plurality of solution chambers, a channel is provided in communication with each of the solution chambers and is directed to the syringe movement cavity, a sealing plug is provided between the channel and the syringe movement cavity and configured to seal therebetween, the syringe is located in the syringe movement cavity at a central axis of the main body, and is rotatable relative to the main body and movable towards or away from a bottom of the main body, the syringe is provided with a puncture needle at an end of the syringe facing the syringe movement cavity, and the puncture needle is not located at a geometric center of a bottom surface of the syringe, and is configured to pierce one of the sealing plugs when the puncture needle is rotated or moved to the sealing plug.

2. The apparatus according to claim 1, wherein the channels are disposed at a bottom the respective solution chambers, and the channels are arranged radially by taking a center of the bottom of the main body as a center.

3. The apparatus according to claim 1, wherein the bottom of the main body is provided with a sample-adding channel, which is configured to load a solution stored in one of the solution chambers for detection.

4. The apparatus according to claim 1, wherein the syringe comprises a syringe cavity, a push-pull rod disposed in the syringe cavity, and a target adsorption material fixedly fitted in the syringe cavity and located between the push-pull rod and the puncture needle in such a manner that the target adsorption material allows a liquid to pass through under a pressure condition and that there is no gap between the target adsorption material and the syringe cavity to prevent the liquid from flowing freely;

the push-pull rod is configured to move the syringe toward the bottom of the main body so that the puncture needle pierces the sealing plug when the push-pull rod is pushed; and is further configured to pump a solution from one of the solution chambers into the syringe cavity through the puncture needle when the push-pull rod is pulled, and the target adsorption material is configured to allow the solution to pass therethrough in both directions.

5. The apparatus according to claim 1, wherein the number of the solution chambers is 2, 3, 4, 5, 6, 7, 8, 9, 10, 11, 12, 13, 14, 15, 16, 17, 18, 19 or 20.

6. The apparatus according to claim 1, wherein the solution chambers are configured for containing the same solution or different solutions.

7. The apparatus according to claim 1, wherein a silicone rubber plug is provided on a top of the plurality of solution chambers.

8. The apparatus according to claim 1, wherein the syringe further comprises a return spring and a sealing ring.

9. The apparatus according to claim 4, wherein the target adsorption material is a material that can adsorb nucleic acid.

10. The apparatus according to claim 4, wherein the target adsorption material is a material that can adsorb protein.

11. The apparatus according to claim 4, wherein the target adsorption material is in the form of a filter element or particles.

12. The apparatus according to claim 11, wherein the target adsorption material is in the form of particles, the syringe is provided with a filter screen at a position near the puncture needle, and the filter screen is configured to obstruct the particulate adsorption material from entering the puncture needle.

13. The apparatus according to claim 3, further comprising a reaction tube, wherein the reaction tube is communicated with the sample-adding channel.

14. The apparatus according to claim 13, wherein the reaction tube is pre-filled with a reaction reagent.

15. The apparatus according to claim 7, wherein a silicone rubber cap is provided on the top of the solution chambers, and a plurality of the silicone rubber plugs are disposed on the silicone rubber cap, and are annularly arranged on a plane.

16. The apparatus according to claim 9, wherein the target adsorption material is configured to be a silica gel membrane or a glass fiber membrane.

17. The apparatus according to claim 14, wherein the reaction reagent comprises a reagent that can be used for a PCR reaction or an isothermal reaction.

\* \* \* \* \*